(12) United States Patent
 Aoki

(10) Patent No.: US 10,112,338 B2
(45) Date of Patent: Oct. 30, 2018

(54) BLOW MOLDING DEVICE

(71) Applicant: MITSUBISHI HEAVY INDUSTRIES MACHINERY SYSTEMS, LTD., Hyogo (JP)

(72) Inventor: Koichi Aoki, Nagoya (JP)

(73) Assignee: MITSUBISHI HEAVY INDUSTRIES MACHINERY SYSTEMS, LTD., Kobe-Shi, Hyogo (JP)

( * ) Notice: Subject to any disclaimer, the term of this patent is extended or adjusted under 35 U.S.C. 154(b) by 134 days.

(21) Appl. No.: 15/022,208

(22) PCT Filed: Sep. 18, 2013

(86) PCT No.: PCT/JP2013/075170
§ 371 (c)(1),
(2) Date: Mar. 16, 2016

(87) PCT Pub. No.: WO2015/040698
PCT Pub. Date: Mar. 26, 2015

(65) Prior Publication Data
US 2016/0229108 A1 Aug. 11, 2016

(51) Int. Cl.
 *B29C 49/46* (2006.01)
 *B29C 49/12* (2006.01)
 (Continued)

(52) U.S. Cl.
 CPC .............. *B29C 49/46* (2013.01); *B29C 49/12* (2013.01); *B29C 49/6418* (2013.01);
 (Continued)

(58) Field of Classification Search
 CPC ............ B29C 49/46; B29C 2049/4682; B29C 2049/4685; B29C 2049/4694
 See application file for complete search history.

(56) References Cited

U.S. PATENT DOCUMENTS 8,083,512 B2 * 12/2011 Adriansens ............... A61L 2/04
 422/303
9,272,060 B2 * 3/2016 Humele .................... A61L 2/12
 (Continued)

FOREIGN PATENT DOCUMENTS

CN 102099253 A 6/2011
EP 2295324 A1 3/2011
 (Continued)

OTHER PUBLICATIONS

Office Action in CN Application No. 201380079623.6, dated Dec. 21, 2016.
 (Continued)

*Primary Examiner* — Robert B Davis
(74) *Attorney, Agent, or Firm* — Kanesaka Berner and Partners LLP

(57) ABSTRACT

The blow molding device (1) is provided with a heating means (4) for heating a preform (P) to a temperature appropriate for molding, an antimicrobial agent-spraying means (50) for spraying an antimicrobial agent on the preform (P), a hot forming means for stretch blow molding the preform into a bottle (B), and an irradiation device (7) irradiating electromagnetic waves or ultrasonic waves on the bottle. After the heating means (4) has heated the preform (P), the anti-microbial agent-spraying means (50) sprays the anti-microbial agent and sterilizes the preform (P) with hot antimicrobial agent. During subsequent stretch blow molding of the preform (P), the hot forming means performs additional drying of antimicrobial agent retained on the preform (P) in the hot state and additional sterilization. The irradiation device (7) irradiates electromagnetic waves or ultrasonic waves to degrade the anti-microbial agent remaining on the molded bottle (B) and further promote antimicrobial agent drying and sterilization.

4 Claims, 3 Drawing Sheets

(51) Int. Cl.
  *B29C 49/64* (2006.01)
  *B29L 31/00* (2006.01)
  *B29C 49/06* (2006.01)
  *B29C 49/08* (2006.01)
  *B29C 49/28* (2006.01)
(52) U.S. Cl.
  CPC .............. *B29C 49/06* (2013.01); *B29C 49/08* (2013.01); *B29C 49/28* (2013.01); *B29C 49/6409* (2013.01); *B29C 2049/4682* (2013.01); *B29C 2049/4685* (2013.01); *B29L 2031/7158* (2013.01)

(56) References Cited

U.S. PATENT DOCUMENTS

| | | | | |
|---|---|---|---|---|
| 9,327,442 | B2* | 5/2016 | Engelhard | B29C 49/42 |
| 9,718,567 | B2* | 8/2017 | Clusserath | B29C 49/46 |
| 2009/0317506 | A1* | 12/2009 | Adriansens | A61L 2/04 425/103 |
| 2011/0061343 | A1* | 3/2011 | Roithmeier | B29C 49/42 53/452 |
| 2011/0133370 | A1* | 6/2011 | Engelhard | B29C 49/42 264/535 |
| 2011/0272861 | A1* | 11/2011 | Humele | A61L 2/12 264/457 |
| 2014/0157726 | A1* | 6/2014 | Clusserath | B29C 49/46 53/452 |
| 2014/0311095 | A1 | 10/2014 | Hayakawa et al. | |

FOREIGN PATENT DOCUMENTS

| | | | | |
|---|---|---|---|---|
| EP | 2394950 | A1 | 12/2011 | |
| JP | 8-282789 | A | 10/1996 | |
| JP | 10-157713 | A | 6/1998 | |
| JP | 2001-212874 | A | 8/2001 | |
| JP | 2008-183899 | A | 8/2008 | |
| JP | 2010-507503 | A | 3/2010 | |
| JP | 2011-46189 | A | 3/2011 | |
| JP | 2011-527246 | A | 10/2011 | |
| JP | 2013-35562 | A | 2/2013 | |
| WO | 2010/090247 | A1 | 8/2010 | |
| WO | WO-2012104018 | A1 * | 8/2012 | ............ B29C 49/46 |
| WO | 2013/061956 | A1 | 5/2013 | |

OTHER PUBLICATIONS

International Search Report in PCT Application No. PCT/JP2013/075170, dated Oct. 29, 2013.
Written Opinion in PCT Application No. PCT/JP2013/075170, dated Oct. 29, 2013.
Extended European Search Report in EP Application No. 13894020.0 dated Mar. 27, 2017.
Office Action in JP Application No. 2015-537489, dated Jul. 26, 2016.
Zhang Deyi et al., Practical Manual for Petrochemical Hazardous Chemicals, China Petrochemical Press, pp. 338, Jan. 31, 2006.
Song Xiaoping et al., Petroleum Chemical Additives and Petroleum Product Manufacturing Technology, Science and Technical Documentation Press, pp. 220, Oct. 31, 2011.
Sun Zuji et al., National Essential Medicine, People's Medical Publishing House, pp. 692, Aug. 31, 1984.
Zheng Ruiwen et al., Fire Safety Technology, Chemical Industry Press, pp. 145, May 31, 2004.
Office Action for Chinese Application No. 201380079623.6, dated May 10, 2018; 16 pages.

* cited by examiner

BLOW MOLDING DEVICE

TECHNICAL FIELD

The present invention relates to a blow molding device heating a preform to a temperature appropriate for molding and then stretch blow molding the preform into a bottle.

BACKGROUND ART

Blow molding methods and devices according to the prior art include a blow molding method and a blow molding device in which a preform prior to stretch blow molding is sterilized by being exposed to an antimicrobial agent such as hydrogen peroxide and peracetic acid for an aseptic filling response regarding a blow-molded bottle (PTL 1 and 2).

CITATION LIST

Patent Literature

[PTL 1] Japanese Unexamined Patent Application Publication No. 2001-212874 (FIG. 1)
[PTL 2] PCT Japanese Translation Patent Publication No. 2011-527246 (FIG. 1)

SUMMARY OF INVENTION

Technical Problem

In a container molding method according to PTL 1 above, which includes a sterilization process for preform sterilization, a heating process for heating the sterilized preform to a temperature appropriate for molding, and a molding process for stretch blow molding the heated preform into a container, the bottle obtained through the stretch blow molding can respond to aseptic filling by sterilizing gas being in contact with a preform surface in the sterilization process.

In PTL 1 above, however, the sterilizing gas remains on a container surface, and this could result in a state that is not preferable in terms of food hygiene.

The present invention has been made in view of the above-described circumstances, and an object thereof is to provide a blow molding device that allows a molded bottle to be in a completely sterile state with no antimicrobial agent remaining on the bottle after stretch blow molding.

Solution to Problem

According to a first aspect of the present invention, a blow molding device includes heating means for heating a preform to a temperature appropriate for molding, antimicrobial agent-spraying means for spraying the preform with an antimicrobial agent generating active oxygen or hydroxyl radical, hot forming means for stretch blow molding the preform into a bottle, and an irradiation device irradiating the molded bottle with electromagnetic waves such as microwaves and UV waves or ultrasonic waves. After the heating of the preform by the heating means, the anti-microbial agent-spraying means sprays the preform with the anti-microbial agent and sterilizes the preform put into a hot state with the antimicrobial agent. Then, during the stretch blow molding of the preform, the hot forming means additionally dries the antimicrobial agent retained on the preform in the hot state and additionally sterilizes the preform. Simultaneously or later, the irradiation device emits the electromagnetic waves such as the microwaves and the UV waves or the ultrasonic waves to degrade the anti-microbial agent remaining on the molded bottle and further promote the drying of the antimicrobial agent and the sterilization of the preform.

According to a second aspect of the present invention, in the blow molding device according to the first aspect described above, the antimicrobial agent generating the active oxygen or the hydroxyl radical is an antimicrobial agent having hydrogen peroxide or peracetic acid as a main component.

According to a third aspect of the present invention, a blow molding device includes antimicrobial agent-spraying means for spraying a preform with an antimicrobial agent generating active oxygen or hydroxyl radical, heating means for heating the preform to a temperature appropriate for molding, hot forming means for stretch blow molding the preform into a bottle, and an irradiation device irradiating the molded bottle with electromagnetic waves such as microwaves and UV waves or ultrasonic waves. The heating means sterilizes the preform sprayed with the antimicrobial agent by the anti-microbial agent-spraying means before or during the heating by the heating means with the antimicrobial agent put into a hot state by being heated. Then, during the stretch blow molding of the preform, the hot forming means additionally dries the antimicrobial agent retained on the preform in the hot state and additionally sterilizes the preform. Simultaneously or later, the irradiation device emits the electromagnetic waves such as the microwaves and the UV waves or the ultrasonic waves to degrade the anti-microbial agent remaining on the molded bottle and further promote the drying of the antimicrobial agent and the sterilization of the preform.

According to a fourth aspect of the present invention, in the blow molding device according to the third aspect described above, the antimicrobial agent generating the active oxygen or the hydroxyl radical is an antimicrobial agent having hydrogen peroxide or peracetic acid as a main component.

Advantageous Effects of Invention

In the blow molding device according to the above-described aspects of the present invention, the preform is sterilized with the antimicrobial agent in the hot state through the heating by the heating means prior to the stretch blow molding with the preform sprayed with the antimicrobial agent generating the active oxygen or the hydroxyl radical such as the hydrogen peroxide and the peracetic acid. Then, during the stretch blow molding by the hot forming means, the antimicrobial agent retained on the preform is additionally dried in the hot state and the preform is additionally sterilized. Simultaneously or later, the electromagnetic waves such as the microwaves and the UV waves or the ultrasonic waves are emitted by the irradiation device, the antimicrobial agent remaining on the molded bottle is degraded, and the drying of the antimicrobial agent and the sterilization of the preform are further promoted. This configuration allows the molded bottle to be in a completely sterile state with no antimicrobial agent remaining and makes available an aseptic filling response preferable in terms of food hygiene.

DESCRIPTION OF EMBODIMENTS

Hereinafter, embodiments of the present invention will be described in detail with reference to accompanying drawings. The present invention is not limited by these embodiments. Elements constituting the embodiments described below include elements that can be easily assumed by those skilled in the art or elements substantially identical thereto.

(First Embodiment)

A first embodiment of the present invention will be described with reference to FIGS. 1 to 6.

Figure 1:
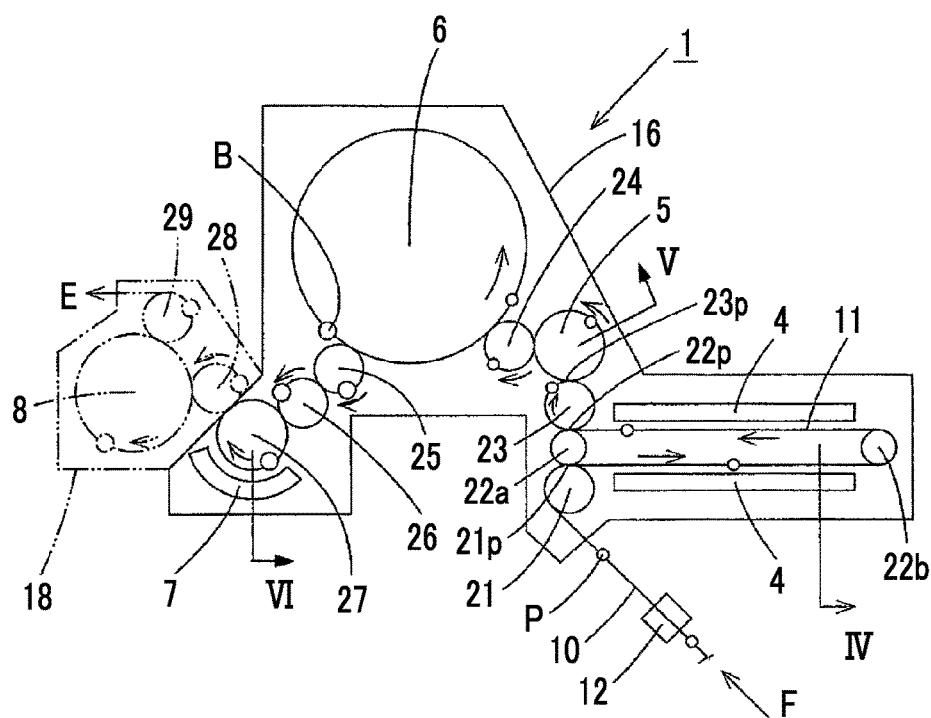
FIG. 1 is a schematic plan view illustrating a blow molding device according to a first embodiment of the present invention.
Figure 2:
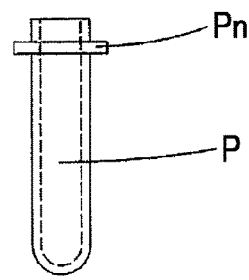
FIG. 2 is a front view of a preform.
Figure 3:
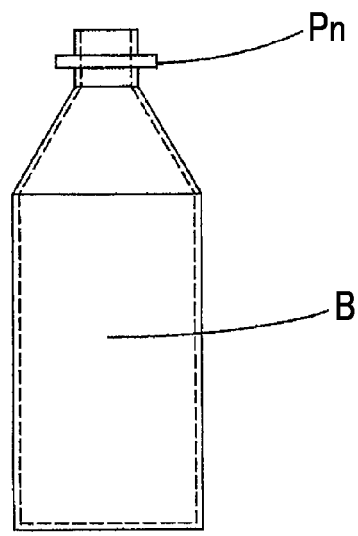
FIG. 3 is a front view of a molded bottle.
Figure 4:
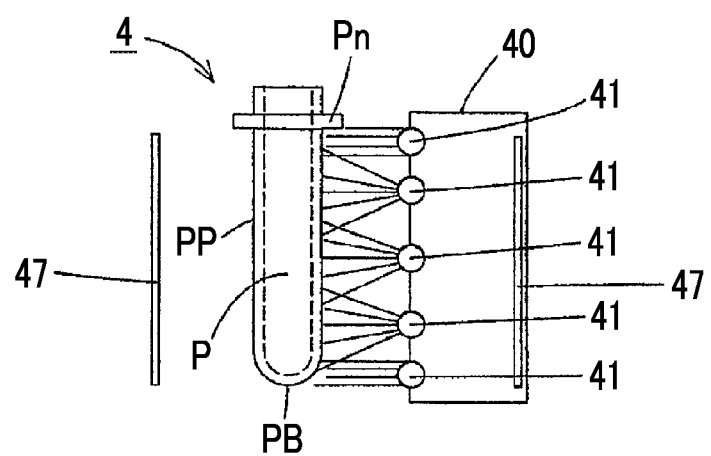
FIG. 4 is an arrow IV view of FIG. 1.
Figure 5:
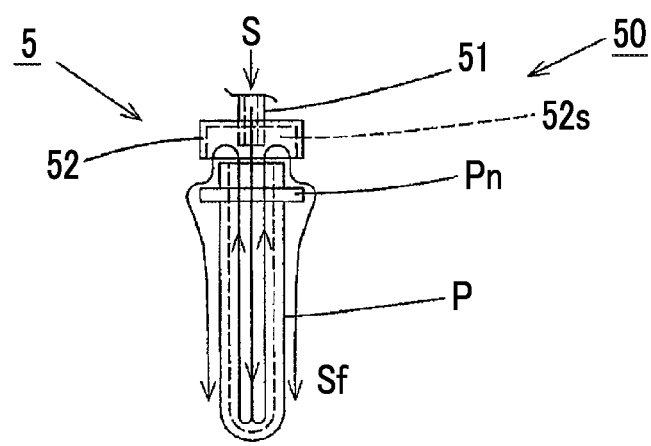
FIG. 5 is an arrow V view of FIG. 1.
Figure 6:
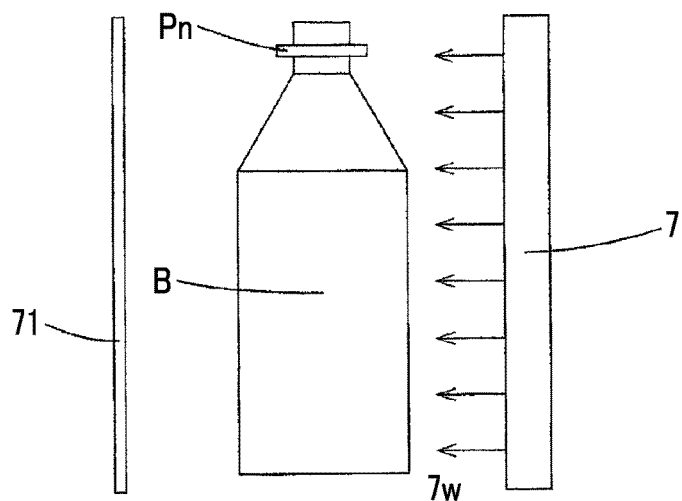
FIG. 6 is an arrow VI view of FIG. 1.

FIG. 1 is a schematic plan view illustrating a blow molding device according to the first embodiment of the present invention. FIG. 2 is a front view of a preform. FIG. 3 is a front view of a molded bottle. FIG. 4 is an arrow IV view of FIG. 1. FIG. 5 is an arrow V view of FIG. 1. FIG. 6 is an arrow VI view of FIG. 1.

Referring to FIG. 1, a blow molding device 1 according to the first embodiment of the present invention is provided with heating means 4, a rotary antimicrobial agent spraying device 5, a rotary blow molding machine 6, and an irradiation device 7. As illustrated in FIG. 2, a preform P that is brought in from an upstream side is sprayed with an antimicrobial agent by the rotary antimicrobial agent spraying device 5 which is provided with antimicrobial agent-spraying means 50 (described later) through the heating means 4 heated to a temperature appropriate for molding during the transport. Then, the rotary blow molding machine 6 that is provided with hot forming means (not illustrated) performs stretch blow molding on a bottle B illustrated in FIG. 3. Then, the molded bottle B is irradiated with electromagnetic waves such as microwaves and UV waves or ultrasonic waves by the irradiation device 7 and is carried out toward an aseptic filling machine 8 that is illustrated by a two-dot chain line in FIG. 1.

A vicinity of a flange portion Pn of the preform P is gripped by a container gripper (not illustrated) disposed at an equal pitch in a transporting apparatus 10, and the preform P is transported in an arrow F direction from the upstream side by the transporting apparatus 10. Then, inner and outer surfaces of the preform P are rinsed by rinse gas in a preform rinser 12, and then the preform P is incorporated into a clean room 16 that has a clean atmosphere. After being incorporated into the clean room 16, the preform P is delivered to a container gripper (not illustrated) that is arranged at an equal pitch in a transporting apparatus 11 at a delivery position 21p of a wheel 21. The transporting apparatus 11 is suspended between a wheel 22a and a wheel 22b and transports the preform P as illustrated by arrows. While being transported by the transporting apparatus 11, the preform P is heated to the temperature appropriate for molding by the heating means 4. Then, the preform P is delivered to a container gripper (not illustrated) that is arranged at a predetermined equal pitch in a rotary transfer star wheel 23 at a delivery position 22p.

Hereinbelow, descriptions as to the delivery positions between the rotary wheels, delivery to the container grippers, and arrangement of the respective container grippers at a predetermined equal pitch will be omitted to avoid repetition.

As illustrated in FIG. 4, the heating means 4 is configured to emit infrared lamp light from a plurality of heating lamps 41 arranged in a heating lamp set 40 to a vertical-direction vicinity of the preform P with the vicinity of the flange portion Pn gripped by the container gripper (not illustrated) and heat a cylindrical portion (shank) PP and a cylinder bottom portion PB of the preform P. Reflective plates 47 are disposed on the heating lamp set 40 side and the side opposite to a surface of the preform P that is heated in the irradiation direction of the heating lamps 41. Accordingly, the preform P can be efficiently heated to the temperature appropriate for molding.

The preform P that is delivered to the transfer star wheel 23 is transported in an arrow direction which is illustrated and is delivered to a container gripper (not illustrated) arranged at a predetermined equal pitch in the rotary antimicrobial agent spraying device 5 at a delivery position 23p. Then, during the rotation transport, the preform P is sprayed with the antimicrobial agent (described later), and is delivered to a container gripper (not illustrated) of the rotary blow molding machine 6 through a transfer star wheel 24. During the rotation transport in the arrow direction that is illustrated, the preform P is subjected to the stretch blow molding in the bottle B illustrated in FIG. 3 by the hot forming means (not illustrated).

As illustrated in FIG. 5, the antimicrobial agent-spraying means 50 of the rotary antimicrobial agent spraying device 5 is disposed to correspond to each of the container grippers (not illustrated), and has a cover 52 that is arranged above a mouth portion of the preform P, a space 52S, and a pipe 51. The pipe 51 is inserted into the space 52S of the cover 52. When the pipe 51 is inserted into the space 52S, the gaseous antimicrobial agent is supplied and sprayed in an arrow S direction from an upstream side of a pipe system (not illustrated). Then, as illustrated by an arrow Sf in the drawing, the gaseous antimicrobial agent is reversed in a bottom portion inside the preform P, rises to the mouth portion, is reversed again in the space 52S of the cover 52, and flows downward on an outer wall side of the preform P. In this manner, the antimicrobial agent-spraying means 50 is configured such that the antimicrobial agent adheres to the entire inner and outer surfaces of the preform P.

An antimicrobial agent that generates active oxygen or hydroxyl radical such as hydrogen peroxide and peracetic acid is selected as the antimicrobial agent.

The bottle B stretch blow molded by the rotary blow molding machine 6 is delivered and transported with the vicinity of the flange portion Pn gripped by container grippers (not illustrated) of a transfer star wheel 25, a transfer star wheel 26, and a star wheel 27 arranged at a predetermined equal pitch. During the rotation transport by the star wheel 27, the bottle B is irradiated with the electromagnetic waves such as the microwaves and the UV waves or the ultrasonic waves by the irradiation device 7.

As illustrated in FIG. 6, the irradiation device 7 irradiates the molded bottle B with the electromagnetic waves such as the microwaves and the UV waves or the ultrasonic waves 7w. A reflective plate 71 is disposed on the side opposite to the irradiation device 7 with respect to the bottle B that is illustrated in a direction in which the electromagnetic waves such as the microwaves and the UV waves or the ultrasonic waves 7w are emitted. Accordingly, the bottle B is efficiently irradiated with the electromagnetic waves such as the microwaves and the UV waves or the ultrasonic waves 7w.

The bottle B that is irradiated with the electromagnetic waves such as the microwaves and the UV waves or the ultrasonic waves 7w by the irradiation device 7 is carried out to the aseptic filling machine 8 through a transfer star wheel 28 in a sterile room 18 which is illustrated by a two-dot chain line in FIG. 1. Then, the bottle B is subjected to aseptic liquid filling, and is discharged in an arrow E direction through a star wheel 29 that has a capping device capping a cap (not illustrated).

Hereinafter, an effect of the blow molding device 1 according to the first embodiment of the present invention will be described.

The preform P illustrated in FIG. 2 is heated to the temperature appropriate for molding by the heating means 4 while being transported and is sprayed with the antimicrobial agent generating the active oxygen or the hydroxyl radical such as the hydrogen peroxide and the peracetic acid by the rotary antimicrobial agent spraying device 5 provided with the antimicrobial agent-spraying means 50 before the stretch blow molding in the bottle B illustrated in FIG. 3 by the rotary blow molding machine 6 provided with the hot forming means. In this case, the preform P is in a hot state as a result of the heating, and thus the inner and outer surfaces are sterilized through degradation of the active oxygen or the hydroxyl radical of the antimicrobial agent. However, some of the sprayed antimicrobial agent might be retained on the preform P.

In the subsequent process, the preform P is subjected to the stretch blow molding in the bottle B illustrated in FIG. 3 by the rotary blow molding machine 6 provided with the hot forming means with some of the sprayed antimicrobial agent being retained. In this case, the antimicrobial agent is dried and the sterilization of the inner and outer surfaces is additionally performed through the degradation of the retained antimicrobial agent in the hot state through the heating by the hot forming means. However, some of the antimicrobial agent might still remain in the bottle B even in this case.

With some of the antimicrobial agent still remaining, the bottle B is irradiated with the electromagnetic waves such as the microwaves and the UV waves or the ultrasonic waves 7w by the irradiation device 7, and then the drying and sterilization of the antimicrobial agent are further promoted through the degradation of the active oxygen or the hydroxyl radical of the remaining antimicrobial agent. Accordingly, the inner and outer surfaces of the bottle B are completely sterilized with no antimicrobial agent remaining, and thus can be subjected to aseptic filling by the aseptic filling machine 8 in the sterile room 18.

(Second Embodiment)

Hereinafter, a second embodiment of the present invention will be described with reference to FIG. 7.

Figure 7:
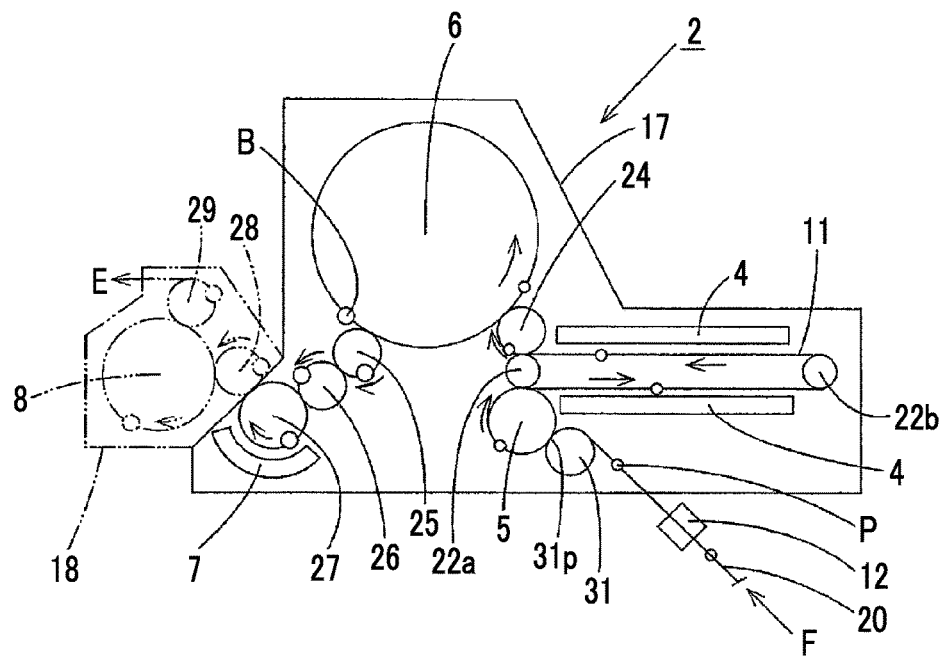
FIG. 7 is a schematic plan view illustrating a blow molding device according to a second embodiment of the present invention.

FIG. 7 is a schematic plan view illustrating a blow molding device according to the second embodiment of the present invention.

The same reference numerals will be used to refer to elements common to FIGS. 1 and 7 so that repetition of description is avoided.

In a blow molding device 2 according to the second embodiment of the present invention, the vicinity of the flange portion Pn of the preform P is gripped by a container gripper (not illustrated) arranged at an equal pitch in a transporting apparatus 20, and the preform P is transported in the arrow F direction from the upstream side by the transporting apparatus 20. Then, the inner and outer surfaces of the preform P are rinsed by the rinse gas in the preform rinser 12, and then the preform P is incorporated into a clean room 17 that has a clean atmosphere. After being incorporated into the clean room 17, the preform P is delivered to the container gripper (not illustrated) that is arranged at an equal pitch in the rotary antimicrobial agent spraying device 5 at a delivery position 31p of a wheel 31 and is sprayed with the antimicrobial agent by the antimicrobial agent-spraying means 50 while being transported. Then, the preform P is delivered to a container gripper (not illustrated) arranged at a predetermined equal pitch in the transporting apparatus 11 transported in an arrow direction in the drawing suspended between the wheel 22a and the wheel 22b. While being transported by the transporting apparatus 11, the preform P is heated to the temperature appropriate for molding by the heating means 4. Then, the preform P is delivered to the transfer star wheel 24 that has a container gripper (not illustrated) arranged at a predetermined equal pitch.

Hereinafter, an effect of the blow molding device 2 according to the second embodiment of the present invention will be described.

The preform P illustrated in FIG. 2 is heated to the temperature appropriate for molding by the heating means 4 while being transported after being sprayed with the antimicrobial agent generating the active oxygen or the hydroxyl radical such as the hydrogen peroxide and the peracetic acid by the rotary antimicrobial agent spraying device 5 provided with the antimicrobial agent-spraying means 50. In this case, the inner and outer surfaces are sterilized through the degradation of the active oxygen or the hydroxyl radical of the antimicrobial agent put into the hot state through the heating by the heating means 4. However, some of the antimicrobial agent might be retained on the preform P.

In the subsequent process, the preform P is subjected to the stretch blow molding in the bottle B illustrated in FIG. 3 by the rotary blow molding machine 6 provided with the hot forming means with some of the sprayed antimicrobial agent being retained. In this case, the antimicrobial agent is dried and the sterilization of the inner and outer surfaces is performed through the degradation of the retained antimicrobial agent in the hot state through the heating by the hot forming means. However, some of the antimicrobial agent might still remain in the bottle B even in this case.

With some of the antimicrobial agent still remaining, the bottle B is irradiated with the electromagnetic waves such as the microwaves and the UV waves or the ultrasonic waves 7w by the irradiation device 7, and then the drying and sterilization are further promoted through the degradation of the active oxygen or the hydroxyl radical of the remaining antimicrobial agent. Accordingly, the inner and outer surfaces of the bottle B are completely sterilized with no antimicrobial agent remaining, and thus can be subjected to the aseptic filling by the aseptic filling machine 8 in the sterile room 18.

In the description of the blow molding device 2 according to the second embodiment of the present invention, a case has been explained where the preform P is sterilized with the antimicrobial agent in the hot state by being heated by the heating means 4 after being sprayed with the antimicrobial agent by the antimicrobial agent-spraying means 50. However, the preform P may also be sterilized with the antimicrobial agent in the hot state by being sprayed with the antimicrobial agent by the antimicrobial agent-spraying means 50 while being heated by the heating means 4. The sterilization of the preform P by the antimicrobial agent in the hot state is similar in content, and thus redundant detailed description will be omitted.

In the description of the blow molding device 1 or the blow molding device 2 according to the first embodiment or the second embodiment of the present invention, a case has been explained where the irradiation device 7 is disposed for a process subsequent to the rotary blow molding machine 6 provided with the hot forming means. However, the irradiation device 7 may be disposed amid the rotary blow molding machine 6 and the bottle B may be subjected to the stretch blow molding by the rotary blow molding machine 6 at the same time as the bottle B is irradiated with the electromagnetic waves such as the microwaves and the UV waves or the ultrasonic waves 7w by the irradiation device 7.

INDUSTRIAL APPLICABILITY

According to this blow molding device, the molded bottle is allowed to be in a completely sterile state with no antimicrobial agent remaining, and an aseptic filling response preferable in terms of food hygiene can be made available.

REFERENCE SIGNS LIST 1, 2 Blow molding device
4 Heating means
41 Heating lamp
5 Rotary antimicrobial agent spraying device
50 Antimicrobial agent-spraying means
6 Rotary blow molding machine (provided with hot forming means)
7 Irradiation device (emitting electromagnetic waves such as microwaves and UV waves or ultrasonic waves)
B Bottle
P Preform

The invention claimed is:

1. A blow molding device comprising:
a heater capable of heating by electromagnetic radiation and configured to heat a preform to a temperature appropriate for molding;
a spraying device having an opening which faces toward the preform and configured to spray the preform with an antimicrobial agent generating active oxygen or hydroxyl radical;
a forming device configured to stretch blow mold forming the preform into a bottle; and
an irradiation device including an ultrasonic waves irradiation portion which irradiates ultrasonic waves and a reflective plate disposed on a side opposite to the ultrasonic waves irradiation portion with respect to the molded bottle,
wherein, after the heater heats the preform, the antimicrobial agent is sprayed from the spraying device, and the heater sterilizes the preform which has become in a hot state by heating,
wherein, after the anti-microbial agent is sprayed, when stretch blow molding the preform in the forming device, the forming device additionally dries the antimicrobial agent retained on the preform in the hot state and additionally sterilizes the preform, and
wherein, simultaneously or after stretch blow molding of the preform, the irradiation device emits the ultrasonic waves to the reflective plate from the ultrasonic waves irradiation portion, and the anti-microbial agent remaining in the molded bottle is decomposed by the ultrasonic waves.

2. The blow molding device according to claim 1, wherein the antimicrobial agent generating the active oxygen or the hydroxyl radical is an antimicrobial agent having hydrogen peroxide or peracetic acid as a main component.

3. A blow molding device comprising:
a spraying device having an opening which faces toward the preform and configured to spray a preform with an antimicrobial agent generating active oxygen or hydroxyl radical;
a heater for heating the preform to a temperature appropriate for molding;
a forming device configured to stretch blow mold forming the preform into a bottle; and
an irradiation device including an ultrasonic waves irradiation portion which irradiates ultrasonic waves and a reflective plate disposed on a side opposite to the ultrasonic waves irradiation portion with respect to the molded bottle,
wherein the heater sterilizes the preform sprayed with the antimicrobial agent by the anti-microbial agent-spraying means before or during the heating by the heating means with the antimicrobial agent put into a hot state by being heated,
wherein, after the anti-microbial agent is sprayed, when stretch blow molding the preform in the forming device the forming device additionally dries the antimicrobial agent retained on the preform in the hot state and additionally sterilizes the preform, and
wherein, simultaneously or after stretch blow molding of the preform, the irradiation device emits the ultrasonic waves to the reflective plate from the ultrasonic waves irradiation portion, and the anti-microbial agent remaining in the molded bottle is decomposed by the ultrasonic waves.

4. The blow molding device according to claim 3, wherein the antimicrobial agent generating the active oxygen or the hydroxyl radical is an antimicrobial agent having hydrogen peroxide or peracetic acid as a main component.

* * * * *